United States Patent
Krumrey et al.

(10) Patent No.: US 10,106,485 B2
(45) Date of Patent: Oct. 23, 2018

(54) PROCESS FOR THE MANUFACTURE OF CARBOXYLIC ANHYDRIDE

(71) Applicant: Rhodia Acetow GmbH, Freiburg (DE)

(72) Inventors: Thomas Krumrey, Teningen (DE); Andreas Hummel, Freiburg (DE); Dirk Hölter, Emmendingen (DE)

(73) Assignee: Rhodia Acetow GmbH, Freiburg (DE)

( * ) Notice: Subject to any disclaimer, the term of this patent is extended or adjusted under 35 U.S.C. 154(b) by 0 days.

(21) Appl. No.: 15/532,306

(22) PCT Filed: Dec. 1, 2015

(86) PCT No.: PCT/EP2015/078160
§ 371 (c)(1),
(2) Date: Jun. 1, 2017

(87) PCT Pub. No.: WO2016/087419
PCT Pub. Date: Jun. 9, 2016

(65) Prior Publication Data
US 2017/0327450 A1    Nov. 16, 2017

(30) Foreign Application Priority Data

Dec. 2, 2014    (EP) .................................... 14195884

(51) Int. Cl.
C07C 51/56    (2006.01)
C07C 51/573   (2006.01)
C07C 49/90    (2006.01)
C07C 11/21    (2006.01)
B27K 5/00     (2006.01)

(52) U.S. Cl.
CPC ............ *C07C 51/56* (2013.01); *B27K 5/0085* (2013.01); *C07C 11/21* (2013.01); *C07C 49/90* (2013.01); *C07C 51/573* (2013.01); *B27K 2240/10* (2013.01)

(58) Field of Classification Search
CPC .................. B27K 5/0085; B27K 2240/10; C07C 51/573; C07C 11/21; C07C 49/90
See application file for complete search history.

(56) References Cited

U.S. PATENT DOCUMENTS

| 2,352,253 A * | 6/1944 | Cockerille | C07C 51/487 |
| | | | 562/898 |
| 8,455,680 B2 * | 6/2013 | Fornara | C07B 41/08 |
| | | | 562/412 |
| 2009/0247788 A1 * | 10/2009 | Warner | C07C 51/46 |
| | | | 562/608 |
| 2009/0275777 A1 | 11/2009 | Fornara et al. | |
| 2013/0197267 A1 | 8/2013 | Warner et al. | |

FOREIGN PATENT DOCUMENTS

DE        663507 C        8/1938
DE        2423079 A1 *    11/1975

OTHER PUBLICATIONS

Fisher et al, Journal of Organic Chemistry, Apparatus for the Preparation of Ketene by the Pyrolysis of Acetic Anhydride, 1953, 18 (8), pp. 1055-1057. (Year: 1953).*
Zaragoza Dorwald, Side Reactions in Organic Synthesis, 2005, WILEY-VCH Verlag GmbH & Co. KGaA, Weinheim, Preface. p. IX . (Year: 2005).*

* cited by examiner

*Primary Examiner* — Paul A Zucker
(74) *Attorney, Agent, or Firm* — Michael Best & Friedrich LLP

(57) ABSTRACT

The present invention concerns a process for manufacturing a fraction comprising carboxylic acid anhydride by reaction of a fraction comprising carboxylic acid with a ketene, and the use of the fraction comprising carboxylic acid anhydride in a process for acylation of polysaccharides.

17 Claims, No Drawings

PROCESS FOR THE MANUFACTURE OF CARBOXYLIC ANHYDRIDE

This application claims priority to European application No. 14195884.3, the whole content of this application being incorporated herein by reference for all purposes.

The present invention concerns a process for manufacturing a fraction comprising carboxylic acid anhydride by reaction of a fraction comprising carboxylic acid with a ketene, and the use of the fraction comprising carboxylic acid anhydride in a process for acylation of polysaccharides.

Carboxylic anhydride is commonly used as acylation agent of polysaccharides, including polysaccharide-containing substances such as wood. Acylated, in particular acetylated, wood is useful e.g. as construction material presenting high service life and excellent resistance against environmental conditions and pathogens. A wood acetylation process is described, for example, in EP 680810 whose relevant contents are incorporated by reference into the present patent application. The economic success of acylation of polysaccharides, in particular acetylation of wood, relies strongly on the recovery of the carboxylic acid which is the by-product of such an acylation process, and the further recycling of said carboxylic acid into the acylation agent, in particular the carboxylic anhydride employed in the acylation of the polysaccharides.

In order to enhance the efficiency and overall economics of acylation processes using carboxylic acid derivatives such as the aforesaid wood treatment process, the present invention now proposes a process for the manufacture of a fraction comprising carboxylic acid anhydride.

US2009/0275777 describes a process for producing carboxylic acid employing solvent from esterification of lignocellulosic material. In [0024-0025], optionally fresh acetic acid can be combined with acetic acid recycled from a lignocellulose esterification process before entering a cracking vessel to form ketene.

The present invention concerns a process for manufacturing a fraction comprising carboxylic acid anhydride, preferably acetic anhydride, by reaction of a fraction comprising carboxylic acid, preferably acetic acid, with a ketene, wherein at least one of the following conditions is met:
  I. at least part of the fraction comprising carboxylic acid is a fraction comprising carboxylic acid and terpene and/or terpene derived impurities and/or
  II. at least part of the ketene is manufactured from a fraction comprising carboxylic acid, wherein the fraction comprising carboxylic acid further comprises and terpene and/or terpene derived impurities For condition I., a content of from 5 to 3000 ppm, more particularly of from 5 to 1500 ppm, by weight of terpene and/or terpene derived impurities and/or for condition II., a content of equal to or less than 3000 ppm, more particularly 1500 ppm, by weight of terpene and/or terpene derived impurities. In one aspect of condition II., a content of terpene and/or terpene derived impurities of from 10 to 100 ppm by weight, is most preferred. The invention further concerns a process for the manufacture of treated wood, in particular acetylated wood, comprising the process for the manufacture of a fraction comprising carboxylic acid anhydride. The invention further concerns use of the fraction comprising carboxylic acid anhydride, obtainable by the above-mentioned processes, in a process for acylation of polysaccharides, in particular wherein the process for acylation of polysaccharides is a wood acetylation process.

It has been found, surprisingly, that a fraction comprising carboxylic acid and terpenes and/or terpene derived impurities is suited for the manufacture of a fraction comprising carboxylic anhydride when the fraction comprising carboxylic anhydride, preferably acetic anhydride, is manufactured via the ketene route, in spite of the presence of impurities. Often, the fraction comprising carboxylic acid is an effluent stream of a polysaccharide acylation process, in particular a wood acylation process, even more particularly a wood acetylation process. In a first embodiment, a fraction comprising carboxylic acid and a specified amount of terpene and terpene derived impurities is fed to a thermal treatment process, in particular a cracking process, to produce ketene which can further be reacted with a fraction comprising carboxylic acid to form a fraction comprising carboxylic anhydride. Surprisingly the ketene production proceeds without side-products in unacceptable amounts or nature or unacceptable equipment soiling. In a second embodiment, the fraction comprising carboxylic acid further comprising the specified amount of terpenes and/or terpene derived impurities is used as absorption acid, wherein the term "absorption acid" generally denotes the fraction comprising carboxylic acid which is reacted with ketene to provide a fraction comprising carboxylic acid anhydride, provided to the process to react with ketene to form a fraction comprising carboxylic anhydride. The obtained fraction comprising carboxylic acid anhydride is particularly suited for recycling back to the process from which the fraction comprising carboxylic acid and impurities originates, in particular wood treatment processes. The invention avoids laborious removal of terpene and terpene derived impurities from the fraction comprising carboxylic acid before the reaction which forms a fraction comprising carboxylic anhydride. In another aspect, a reduction of terpenes and/or terpene derived impurities in the fraction comprising carboxylic acid and a specified amount of terpenes and/or terpene derived impurities before further feeding the fraction, be it as absorption acid or ketene precursor fraction, to the process of manufacturing the fraction comprising carboxylic acid anhydride can be advantageous.

In the present invention the fraction comprising carboxylic acid, in particular acetic acid, often originates from industrial processes such as, for example, acetylation of polysaccharides such as wood treatment processes. Preferably, the fraction comprising carboxylic acid originates from a wood treatment process, in particular a wood acetylation process. In the process according to the invention, the carboxylic acid is preferably selected from the group of straight or branched C2 to C7 alkyl or alkylene carboxylic acids of the formula $R^3COOH$, wherein $R^3$ is selected from the group consisting of straight or branched C1 to C6 alkyl or alkylene groups which can optionally be substituted, for example by at least one substituent selected from the group of halogens, OH and CN, and/or which can optionally be unsaturated. Preferably, the carboxylic acid is selected from the group consisting of acetic acid, trifluoroacetic acid, propionic acid, n-butyric acid, iso-butyric acid and acrylic acid. Acetic acid is the most preferred carboxylic acid.

In the process according to the invention, the fraction comprising carboxylic acid often comprises terpenes and/or terpene derived impurities. "Terpene derived impurities" often are also denoted as "terpenoids". Specific examples of terpenes and terpenoids include terpinenes, terpinolenes, α-terpineol acetate, α-fenchene, camphene, p-methyl isopropyl benzene (p-cymene), limonenes, α-fenchyl acetate, isobornyl acetate, α-pinene, β-pinene and pinocarvyl acetate. Other terpenes and terpenoids can also be comprised in the fraction. The amount of terpenes and terpenoid impurities can be determined by GC-MS. A suitable GC-MS measurement protocol is described as follows: The sample is analysed with combined GC Agilent 7890 and MS Agilent MSD 5975. For the GC, a capillary Wax column (for example Zebron™ ZB-Wax) (length=60 cm, diameter: 0.32 mm, df=0.5 µm, wherein df=film thickness), flow 1.2 mL/min is used, running with a temperature gradient of 40° C. (6 min)->10° C./min->250° C. As standard, a solution of target impurities in acetic acid is used, also for column calibration.

In one embodiment of the present invention, "ketene" denotes substances of the structure $R^1R^2C=C=O$, wherein $R^1$ and $R^2$ independently can be hydrogen, alkyl or alkylene which can optionally be branched and/or substituted, in particular wherein $R^1$ and $R^1$ can be the same as $R^3$, aryl, acyl and halogen.

According to a most preferred embodiment of the present invention, the term "ketene" is intended to denote the compound of the formula $H_2C=C=O$, with $R^1$ and $R^2$ being H.

Carboxylic anhydrides, according to the present invention, denote compounds consisting of two acyl groups bonded to the same oxygen atom, which can be denoted as $R^1R^2HC-C(O)-O-C(O)-R^3$, wherein $R^3$, $R^1$ and $R^2$ are the same as described above. In the present invention, $R^1$ and $R^2$ preferably are H, straight or branched C1 to C6 alkyl, in particular linear C1-C4 alkyl or branched C3-C6 alkyl, or unsaturated C3-C6 alkyl, wherein alkyl can optionally be substituted by at least one substituent selected from the group consisting of halogen atoms, in particular fluorine, OH and CN. Acetic anhydride, with both $R^1$ and $R^2$ being H, is preferred according to the present invention. The fraction comprising carboxylic acid can also be a mixture of two or more carboxylic acids. In this case, firstly asymmetrical carboxylic anhydrides can form in the process according to the present invention. Secondly, different ketene species can form when a mixture of two or more carboxylic anhydrides are subjected to thermal treatment, in particular cracking. In another aspect, asymmetric carboxylic acid anhydrides are formed if $R^1 R^2C=C=O$ is reacted with $R^3COOH$, when $R^1R^2HC \neq R^3$.

In a very preferred embodiment of the present invention, a fraction comprising carboxylic anhydride is formed by reaction of ketene with a fraction comprising carboxylic acid. The ketene preferably is formed by thermal treatment, also denoted as "cracking", of carboxylic acid, in particular acetic acid.

In one embodiment, the ketene is provided by thermal cracking of a fraction comprising carboxylic acid, in particular acetic acid, and further comprising terpenes and/or terpene derived impurities. This embodiment corresponds to condition II. The basic technique of thermal cracking of carboxylic acid, in particular acetic acid, is known in the art, as described in "Ketenes, Ketene Dimers, and Related Substances", Taeschler, C, Kirk-Othmer Encyclopedia of Chemical Technology, p. 1-54, 2010, whose relevant contents are incorporated by reference into the present patent application. Taeschler recites that for the thermal cracking high quality acetic acid is evaporated and cracked, while the present embodiment allows for terpene and terpene derived impurities to be present in the ketene production step. According to the present embodiment, the fraction comprising acetic acid and terpenes and/or terpene derived impurities is heated in a suitable cracking furnace in the presence of a catalyst, such as triethyl phosphate. The cracking temperature often is from 500° C. to 800° C., preferably from 720° C. to 780° C. The cracking furnace is made of suitable, heat resistant material, for example Sicromal comprising 25% Cr, 20% Ni, and 2% Si. Often, the formed ketene stream is treated with a neutralization agent such as ammonia to neutralize the catalyst. In a preferred aspect of this embodiment, the ketene stream is first cooled to less than 100° C. before being fed to the subsequent reaction step, which is preferentially a reaction with a fraction comprising carboxylic acid. This makes removal of water, unconverted carboxylic acid and other by-products possible.

In a preferred aspect of the present invention, the ketene is formed in a first reaction zone, which preferably has a temperature of from 500° C. to 800° C., preferably from 720° C. to 780° C., and then the ketene is reacted with a fraction comprising carboxylic acid to form carboxylic anhydride in a second reaction zone. Generally, the temperature of the second reaction zone is from 10° C. to 100° C. In another aspect of the invention, the ketene is reacted with carboxylic acid to form carboxylic anhydride in the same reaction zone. In this embodiment, the fraction comprising carboxylic acid and terpenes and/or terpene derived impurities which is used to generate ketene generally contains from equal to or less than 3000 ppm by weight terpenes and/or terpene derived impurities. Preferably, the content of terpenes and/or terpene derived impurities in the fraction comprising carboxylic acid is equal to or lower than 1500 ppm by weight. More preferably, the content of terpenes and/or terpene derived impurities in the fraction comprising carboxylic acid is equal to or lower than 1300 ppm by weight. Even more preferably, the content of terpenes and/or terpene derived impurities in the fraction comprising carboxylic acid is equal to or lower than 1000 ppm by weight. Most preferably, the content of terpenes and/or terpene derived impurities in the fraction comprising carboxylic acid is equal to or lower than 700 ppm by weight. The amount of impurities can be determined by GC-MS, by the method described above. In another aspect of this embodiment, a content of terpenes and/or terpene derived impurities in the fraction comprising carboxylic acid from which ketene is formed by thermal treatment of equal to or more than 10 ppm, or even equal to or more than 20 ppm is tolerated.

If the ketene is manufactured by thermal cracking of a fraction comprising carboxylic acid and terpenes and/or terpene derived impurities, the fraction can be supplied to the thermal cracking step directly from the process in which the fraction comprising carboxylic acid and terpenes and/or terpene derived impurities is generated, in particular from a wood acetylation process. In one aspect, which is preferred, the fraction comprising carboxylic acid and terpenes and/or terpene derived impurities is submitted to at least one intermediate treatment step, in particular a purification step, prior to the cracking process. The at least one purification step preferably is selected from the group consisting of decantation, stripping, spinning, filtration, evaporation, condensation, steam treatment and treatment with an additive, for example an aqueous phase and/or a metal salt. In a preferred aspect of the invention, the purification of the fraction comprising carboxylic acid and terpene and terpene derived impurities comprises a) treating the fraction comprising carboxylic acid and terpene and terpene derived impurities with a metal salt in the presence of water
b) treating at least part of the fraction obtained from step a) to remove metal salt and optionally
c) treating at least part of the fraction obtained from step b) by at least one operation selected from the group of operations consisting of distillation, stripping or membrane separation to recover at least a purified carboxylic acid fraction.

The metal salt often is a basic metal salt, such as alkaline earth acetate or hydroxide or alkaline acetate or hydroxide. A preferred metal salt is sodium acetate or sodium hydroxide. In yet another embodiment of the present invention, the ketene which is fed to the process for manufacturing a fraction comprising carboxylic acid anhydride is manufactured by thermal cracking of a fraction comprising carboxylic acid, wherein the fraction comprising carboxylic acid is free or substantially free of terpenes and/or terpene derived impurities, wherein "substantially free" denotes a content of terpenes and/or terpene derived impurities in the fraction of equal to or less than 9 ppm by weight, preferably equal to or less than 7 ppm by weight, and even more preferably equal to or less than 5 ppm by weight. In another aspect, the fraction comprising carboxylic acid contains equal to or less than 1000 ppm by weight, preferably equal to or less than 500 ppm by weight and most preferably equal to or less than 300 ppm by weight of other impurities. The amount of terpenes and/or terpene derived and other impurities can be determined by GC-MS, by the method described above. In a preferred aspect of the embodiment, the ketene is formed in a first reaction zone, which preferably has a temperature of from 500° C. to 800° C., preferably from 720° C. to 780° C., and then the ketene is reacted with a fraction comprising carboxylic acid to form carboxylic anhydride in a second reaction zone. Generally, the temperature of the second reaction zone is from 10° C. to 100° C. In another aspect of the invention, the ketene is reacted with carboxylic acid to form carboxylic anhydride in the same reaction zone.

In a further embodiment of the present invention, the ketene which is fed to the process for manufacturing a fraction comprising carboxylic acid anhydride is manufactured by other ketene manufacturing processes, for example reaction of the corresponding carboxylic acid anhydride bearing at least one hydrogen atom at position α with a base, or by Wolff rearrangement of α-diazoketones.

In another embodiment, the fraction comprising carboxylic acid and terpenes and/or terpene derived impurities is reacted with ketene to form a fraction comprising carboxylic anhydride. This embodiment corresponds to condition I. Often, the fraction comprising carboxylic acid and terpenes and/or terpene derived impurities is also denoted as "absorption acid". In this embodiment, the fraction comprising carboxylic acid and terpenes and/or terpene derived impurities generally contains from 55 to 3000 ppm by weight terpenes and/or terpene derived impurities. Often, the content of terpenes and/or terpene derived impurities in the fraction comprising carboxylic acid is equal to or higher than 5 ppm by weight. Preferably, the content of terpenes and/or terpene derived impurities in the fraction comprising carboxylic acid is equal to or higher than 10 ppm by weight. More preferably, the content of terpenes and/or terpene derived impurities in the fraction comprising carboxylic acid is equal to or higher than 15 ppm by weight. Most preferably, the content of terpenes and/or terpene derived impurities in the fraction comprising carboxylic acid is equal to or higher than 20 ppm by weight. Often, the content of terpenes and/or terpene derived impurities in the fraction comprising carboxylic acid is equal to or lower than 3000 ppm by weight. Preferably, the content of terpenes and/or terpene derived impurities in the fraction comprising carboxylic acid is equal to or lower than 1500 ppm by weight. More preferably, the content of terpenes and/or terpene derived impurities in the fraction comprising carboxylic acid is equal to or lower than 1300 ppm by weight. Even more preferably, the content of terpenes and/or terpene derived impurities in the fraction comprising carboxylic acid is equal to or lower than 1000 ppm by weight Most preferably, the content of terpenes and/or terpene derived impurities in the fraction comprising carboxylic acid is equal to or lower than 700 ppm by weight. In a preferred aspect, the content of terpenes and/or terpene derived impurities in the fraction comprising carboxylic acid which is fed to the process as absorption acid is from 10 to 100 ppm, more preferably from 10 to 50 ppm. The amount of impurities can be determined by GC-MS, by the method described above.

In yet another embodiment of the present invention, the fraction comprising carboxylic acid which is fed to the process of the present invention as absorption acid to react with ketene, wherein the fraction comprising carboxylic acid is free or substantially free of terpenes and/or terpene derived impurities, wherein "substantially free" denotes a content of terpenes and/or terpene derived impurities in the fraction of equal to or less than 9 ppm by weight, preferably equal to or less than 7 ppm by weight, and even more preferably equal to or less than 5 ppm by weight. In another aspect, the fraction comprising carboxylic acid contains equal to or less than 1000 ppm by weight, preferably equal to or less than 500 ppm by weight and most preferably equal to or less than 300 ppm by weight of other impurities. The amount of impurities can be determined by GC-MS, by the method described above.

The fraction comprising carboxylic acid and terpenes and/or terpene derived impurities which is reacted with ketene as absorption acid can be supplied to the reaction with ketene directly from the process in which the fraction comprising carboxylic acid and terpenes and/or terpene derived impurities is generated, in particular from a wood acetylation process. Preferably, the fraction comprising carboxylic acid and terpenes and/or terpene derived impurities is submitted to at least one intermediate treatment step, preferably a purification step, prior to the reaction with ketene. The at least one purification step preferably is selected from the group consisting of decantation, stripping, spinning, filtration, evaporation, condensation, steam treatment and treatment with an additive, for example an aqueous phase and/or a metal salt. In a preferred aspect of the invention the intermediate treatment of the fraction comprising carboxylic acid and terpene and terpene derived impurities is a purification which comprises
  a) treating the fraction comprising carboxylic acid and terpene and terpene derived impurities with a metal salt in the presence of water
  b) treating at least part of the fraction obtained from step a) to remove metal salt and optionally
  c) treating at least part of the fraction obtained from step b) by at least one operation selected from the group of operations consisting of distillation, stripping or membrane separation to recover at least a purified carboxylic acid fraction.

The purified carboxylic acid fraction obtained by step c) can be supplied to the cracking step to obtain ketene and/or to the carboxylic anhydride manufacturing process as absorption acid. The metal salt often is a basic metal salt, such as alkaline earth acetate or hydroxide or alkaline acetate or hydroxide. The preferred metal salt in step b) is sodium acetate and/or sodium hydroxide.

In one aspect of the invention, the fraction comprising carboxylic acid and terpenes and/or terpene derived impurities is supplied both to the cracking step to form ketene and to the reaction step with the ketene as absorption acid to form the fraction comprising carboxylic acid anhydride. In other words, conditions I. and II. are met simultaneously, wherein in condition I., at least part of the fraction comprising carboxylic acid, which is reacted with ketene to manufacture a fraction comprising carboxylic anhydride, is a fraction comprising carboxylic acid and terpene and/or terpene derived impurities, in particular from 5 to 3000 ppm by weight, more particularly from 5 to 1500 ppm, most particularly from 10 to 100 ppm by weight of terpene and/or terpene derived impurities, and wherein in condition II. at least part of the ketene is manufactured from a fraction comprising carboxylic acid, wherein the fraction comprising carboxylic acid further comprises terpene and/or terpene derived impurities, in particular equal to or less 3000 ppm, more particularly 1500 ppm by weight of terpene and/or terpene derived impurities, and wherein the ketene is manufactured by a thermal treatment process. In one aspect of condition II., a content of terpene and/or terpene derived impurities of from 10 to 100 ppm by weight, is most preferred. The fractions comprising carboxylic acid and terpenes and/or terpene derived impurities independently in condition I. and II. can be used directly from their originating process, in particular wood acetylation process, or can be submitted to one or more purifications steps such as described above.

The process according to the invention and its specific aspects and embodiments of the present invention can suitably be run batch-wise or continuously, and/or can be part of another batch-wise or continuous process comprising further steps.

The invention further concerns a process for the manufacture of treated wood, in particular acetylated wood, comprising the process for the manufacture of a fraction comprising carboxylic acid anhydride according to the foregoing embodiments.

The invention also concerns the use of carboxylic anhydride, in particular acetic anhydride, obtainable by the process according to the foregoing embodiments, in a process for acylation of polysaccharides. Preferably, the process for acylation of polysaccharides is a wood acetylation process.

Should the disclosure of patents, patent applications and publications which are incorporated herein by reference conflict with the description of the present application to the extent that it may render a term unclear, the present description shall take precedence.

Should the disclosure of any patents, patent applications, and publications which are incorporated herein by reference conflict with the description of the present application to the extent that it may render a term unclear, the present description shall take precedence.

The examples which follow are intended to illustrate the present invention without, however, limiting the scope thereof.

EXAMPLE

An acetic acid fraction, produced as effluent stream from a wood acetylation process, is filtered and distilled to yield a purified acetic acid fraction -with a content of terpene and/or terpene derived impurities of about 40 ppm by weight. The purified acetic acid is reacted as absorption acid with ketene, which is produced in a first reaction zone at about 730° C. from acetic acid in the presence of triethyl phosphate, in a second reaction zone at a temperature of 25 to 60° C. to yield a fraction comprising acetic anhydride.

The invention claimed is:

1. A process for manufacturing a composition comprising carboxylic acid anhydride by reaction of a composition comprising carboxylic acid with a ketene, wherein at least one of the following conditions is met:
   I. at least part of the composition comprising carboxylic acid is a composition comprising carboxylic acid and terpene and/or terpenoids; and/or
   II. at least part of the ketene is manufactured from a composition comprising carboxylic acid, wherein the composition comprising carboxylic acid further comprises terpene and/or terpenoids,
   wherein the carboxylic acid in II is selected from carboxylic acids of the formula $R^3COOH$, wherein $R^3$ is selected from the group consisting of straight or branched C1 to C6 alkyl groups which can be optionally substituted by at least one halogen wherein the composition comprising carboxylic acid in condition I comprises from 5 to 3000 ppm by weight of terpene and/or terpenoids, and/or wherein the composition comprising carboxylic acid in condition II comprises equal to or less than 3000 ppm by weight of terpene and/or terpenoids.

2. The process according to claim 1, wherein the carboxylic acid anhydride is acetic anhydride.

3. The process according to claim 1, wherein the composition comprising carboxylic acid and terpene and/or terpenoids originates from a wood treatment process.

4. The process according to claim 1, wherein the carboxylic acid is selected from the group consisting of acetic acid, trifluoroacetic acid, propionic acid, n-butyric acid, iso-butyric acid, and acrylic acid.

5. The process according to claim 1, wherein the carboxylic acid is acetic acid.

6. The process according to claim 1, wherein condition II is met, and wherein the ketene is manufactured by a thermal treatment process.

7. The process according to claim 1, wherein the ketene is manufactured in a first reaction zone, and the reaction of ketene with the fraction comprising carboxylic acid is performed in a second reaction zone.

8. The process according to claim 7, wherein the first reaction zone has a temperature of from 500° C. to 800° C., and wherein the second reaction zone has a temperature of from 10° C. to 100° C.

9. The process according to claim 1, wherein the composition comprising carboxylic acid and terpene and/or terpenoids is without intermediate treatment between a process in which the composition comprising the carboxylic acid is generated and the reaction with the ketene or the manufacture of the at least part of the ketene.

10. The process according to claim 1, wherein the composition comprising carboxylic acid and terpene and terpenoids is treated in an intermediate treatment step between a process in which the composition comprising the carboxylic acid is generated and the reaction with the ketene or the manufacture of the at least part of the ketene.

11. The process according to claim 10, wherein the intermediate treatment of the composition comprising carboxylic acid and terpene and terpenoids is a purification which comprises:
   a) treating the composition comprising carboxylic acid and terpene and terpenoids with a metal salt in the presence of water,
   b) treating at least part of the composition obtained from step a) to remove metal salt, and optionally,
   c) treating at least part of the composition obtained from step b) by at least one operation selected from the group of operations consisting of distillation, stripping, or membrane separation to recover a purified carboxylic acid composition.

12. A process for the manufacture of treated wood comprising the process for the manufacture of a composition comprising carboxylic acid anhydride according to claim 1.

13. The process according to claim 1, wherein the carboxylic acid anhydride is acetic anhydride.

14. The process according to claim 1, wherein the process comprises acylation of polysaccharides in a wood acetylation process.

15. The process according to claim 9, wherein the composition comprising carboxylic acid and terpene and/or terpenoids is unpurified.

16. The process according to claim 10, wherein the intermediate treatment is selected from the group consisting of evaporation, stripping, filtration, steam treatment, addition of additives, and condensation.

17. The process according to claim 1, wherein the carboxylic acid is selected from the group consisting of acetic acid, propionic acid, n-butyric acid, and iso-butyric acid.

* * * * *